(12) United States Patent
Ternes et al.

(10) Patent No.: US 8,548,593 B2
(45) Date of Patent: Oct. 1, 2013

(54) DISTAL END CONVERTER FOR A MEDICAL DEVICE LEAD

(75) Inventors: David J. Ternes, Roseville, MN (US); Stephen Ruble, Lino Lakes, MN (US); Jason Hamann, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 880 days.

(21) Appl. No.: 12/613,455

(22) Filed: Nov. 5, 2009

(65) Prior Publication Data

US 2010/0121405 A1 May 13, 2010

Related U.S. Application Data

(60) Provisional application No. 61/112,801, filed on Nov. 10, 2008.

(51) Int. Cl.
*A61N 1/36* (2006.01)

(52) U.S. Cl.
USPC ............................................ 607/42; 607/118

(58) Field of Classification Search
USPC .................................. 607/116–118
See application file for complete search history.

(56) References Cited

U.S. PATENT DOCUMENTS

| | | |
|---|---|---|
| 4,573,481 A | 3/1986 | Bullara |
| 4,590,949 A | 5/1986 | Pohndorf |
| 4,602,624 A | 7/1986 | Naples et al. |
| 4,740,170 A | 4/1988 | Lee et al. |
| 4,920,979 A | 5/1990 | Bullara |
| 4,979,511 A | 12/1990 | Terry, Jr. |
| 5,095,905 A | 3/1992 | Klepinski |
| 5,215,089 A | 6/1993 | Baker, Jr. |
| 5,251,634 A | 10/1993 | Weinberg |
| 5,324,322 A * | 6/1994 | Grill et al. ..................... 607/118 |
| 5,334,438 A | 8/1994 | Saugnac |
| 5,351,394 A | 10/1994 | Weinberg |
| 5,505,201 A | 4/1996 | Grill, Jr. et al. |
| 5,531,778 A | 7/1996 | Maschino et al. |
| 5,674,272 A | 10/1997 | Bush et al. |
| 5,689,877 A | 11/1997 | Grill, Jr. et al. |

(Continued)

FOREIGN PATENT DOCUMENTS

| | | |
|---|---|---|
| WO | WO 2008/088798 | 7/2008 |
| WO | WO 2009025817 | 2/2009 |

OTHER PUBLICATIONS

International Search Report and Written Opinion Issued in PCT/US2010/026350, mailed Jun. 2, 2010.

(Continued)

*Primary Examiner* — Carl H Layno
*Assistant Examiner* — Jon Eric C Morales
(74) *Attorney, Agent, or Firm* — Faegre Baker Daniels, LLP (57) ABSTRACT

A system for delivering signals between a pulse generator and tissue includes a lead having a lead body and one or more lead electrodes at a distal end of the lead body. The one or more electrodes are electrically connectable to the pulse generator at a proximal end of the lead body via one or more conductors extending through the lead body. A converter, which is removably securable to the distal end of the lead body, includes one or more converter electrodes. Each converter electrode is connected to an electrical contact that is arranged on the converter to electrically connect the converter electrode to at least one of the one or more lead electrodes.

21 Claims, 7 Drawing Sheets

(56) References Cited

U.S. PATENT DOCUMENTS

| | | |
|---|---|---|
| 5,782,892 A | 7/1998 | Castle et al. |
| 5,964,702 A | 10/1999 | Grill, Jr. et al. |
| 6,038,479 A | 3/2000 | Werner et al. |
| 6,051,017 A | 4/2000 | Loeb et al. |
| 6,093,197 A | 7/2000 | Bakula et al. |
| 6,178,349 B1 | 1/2001 | Kieval |
| 6,292,703 B1 | 9/2001 | Meier et al. |
| 6,600,956 B2 | 7/2003 | Maschino et al. |
| 6,725,096 B2 | 4/2004 | Chin et al. |
| 7,047,081 B2 | 5/2006 | Kuzma |
| 7,561,923 B2 | 7/2009 | Libbus et al. |
| 7,933,662 B2 | 4/2011 | Marshall et al. |
| 2003/0040785 A1 | 2/2003 | Maschino et al. |
| 2004/0010303 A1* | 1/2004 | Bolea et al. .................. 607/118 |
| 2004/0111139 A1 | 6/2004 | McCreery |
| 2006/0122675 A1 | 6/2006 | Libbus et al. |
| 2006/0259078 A1 | 11/2006 | Libbus |
| 2007/0118177 A1 | 5/2007 | Libbus et al. |
| 2007/0142871 A1 | 6/2007 | Libbus et al. |
| 2007/0255320 A1 | 11/2007 | Inman et al. |
| 2008/0051839 A1 | 2/2008 | Libbus et al. |
| 2008/0058871 A1 | 3/2008 | Libbus et al. |
| 2008/0058874 A1 | 3/2008 | Westlund et al. |
| 2008/0058901 A1 | 3/2008 | Ternes et al. |
| 2008/0086181 A1 | 4/2008 | Amurthur et al. |
| 2008/0091255 A1 | 4/2008 | Caparso et al. |
| 2008/0103545 A1* | 5/2008 | Bolea et al. .................. 607/42 |
| 2008/0172101 A1 | 7/2008 | Bolea et al. |
| 2008/0177365 A1 | 7/2008 | Bolea et al. |
| 2008/0183258 A1 | 7/2008 | Inman |
| 2008/0195188 A1 | 8/2008 | Libbus |
| 2008/0234780 A1 | 9/2008 | Smith et al. |
| 2009/0048641 A1 | 2/2009 | Libbus |
| 2010/0305674 A1 | 12/2010 | Zarembo et al. |
| 2012/0065702 A1 | 3/2012 | Arcot-Krishnamurthy et al. |

OTHER PUBLICATIONS

International Search Report and Written Opinion Issued in PCT/US2009/063442, mailed Jan. 1, 2010, 11 pages.

International Search Report and Written Opinion Issued in PCT/US2011/049585, mailed Dec. 19, 2011.

\* cited by examiner

DISTAL END CONVERTER FOR A MEDICAL DEVICE LEAD

CROSS-REFERENCE TO RELATED APPLICATION

This application claims priority under 35 U.S.C. §119 to U.S. Provisional Application No. 61/112,801, filed on Nov. 10, 2008, entitled "Distal End Converter for a Medical Device Lead," which is incorporated herein by reference in its entirety for all purposes.

TECHNICAL FIELD

The present invention relates generally to implantable medical devices. More specifically, the present invention relates to a converter for modifying the electrode arrangement of a medical device lead.

BACKGROUND

A significant amount of research has been directed both to the direct and indirect stimulation and sensing of the left and right vagus nerves, the phrenic nerve, the sacral nerve, the cavernous nerve, and portions of the anatomy with baroreceptors (e.g., the carotid artery) to treat a wide variety of medical, psychiatric, and neurological disorders or conditions. For example, stimulation of the vagus nerve has been proposed as a method for treating various heart conditions, including heart failure. The nerves stimulated and/or sensed may be sympathetic or parasympathetic in character.

In a nerve stimulation and sensing system, one or more electrodes are formed on a lead that are electrically connected to an implanted electronic package, such as a pulse generator. Electrical energy is delivered to the electrodes by conductors that extend from the pulse generator at a proximal end of the lead to the electrodes at a distal end of the lead. For direct stimulation of a nerve, the electrodes may be configured to be secured directly to, wrapped around, or laid next to the nerve.

SUMMARY

In one aspect, the present invention relates to a system for delivering signals between a pulse generator and tissue. The system includes a lead having a lead body and one or more lead electrodes at a distal end of the lead body. The one or more electrodes are electrically connectable to the pulse generator at a proximal end of the lead body via one or more conductors extending through the lead body. A converter, which is removably securable to the distal end of the lead body, includes one or more converter electrodes. Each converter electrode is connected to an electrical contact that is arranged on the converter to electrically connect the converter electrode to at least one of the one or more lead electrodes.

In another aspect, the present invention relates to a converter for modifying a configuration of lead electrodes, which are configured to deliver stimulation energy, at a distal end of a medical device lead. The converter includes a converter body removably securable to the distal end of the medical device lead. The converter also includes one or more converter electrodes are coupled to the converter body and one or more electrical contacts. Each electrical contact is arranged to electrically connect one of the one or more converter electrodes to one of the lead electrodes.

In a further aspect, the present invention relates to an implantable medical device including a pulse generator and a lead including a proximal end adapted to be connected to the pulse generator. A distal end of the lead includes one or more lead electrodes adapted to deliver electrical signals from the pulse generator. A converter is removably secured to the distal end of the lead body and includes one or more converter electrodes. Each converter electrode is connected to an electrical contact that is arranged to electrically connect the converter electrode to one of the one or more lead electrodes.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1A:
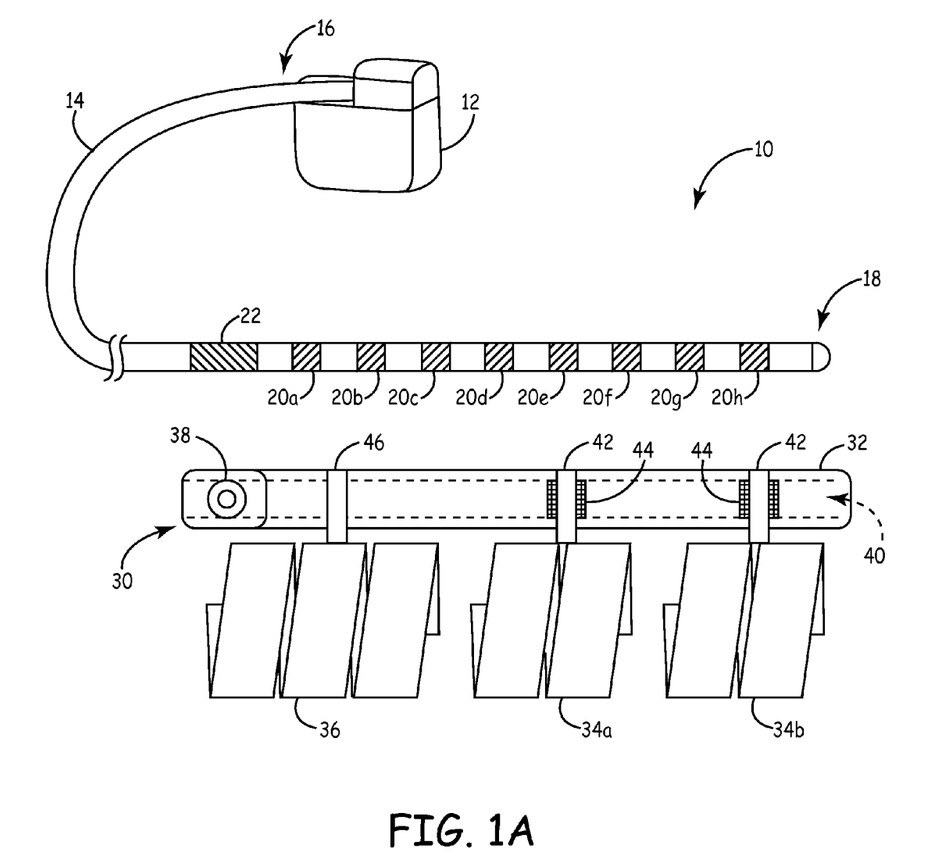
FIG. 1A is a plan view of a system including a lead and a converter securable to the distal end of the lead for modifying the electrode configuration of the lead.

FIG. 1A is a plan view of a system 10 including an implantable medical device (IMD) 12 with a lead 14 having a proximal end 16 and a distal end 18. In one embodiment, the IMD 12 includes a pulse generator. The IMD 12 can be implanted subcutaneously within the body, typically at a location such as in a patient's chest or abdomen, although other implantation locations are possible. The proximal end 16 of the lead 14 can be coupled to or formed integrally with the IMD 12. The distal end 18 of the lead 14, in turn, can be implanted at a desired location in or near the patient's body. In some embodiments, the lead 14 has a round cross-section.

The distal end 18 of the lead 14 includes a plurality of electrodes 20a, 20b, 20c, 20d, 20e, 20f, 20g, and 20h and a retention cuff 22. The electrodes 20 are electrically connected to the IMD 12 via one or more conductors (not shown) extending through the lead 14. During operation, the lead 14 delivers electrical signals between the IMD 12 and the electrodes 20. The electrodes 20 may be separately controlled by IMD 12, such that energy having different magnitude, phase, and/or timing characteristics may be delivered to or from each of the electrodes 20. While the lead 14 shown includes eight electrodes 20*a*-20*h*, it will be appreciated that any number of electrodes having any arrangement on the lead 14 can alternatively be employed in the system 10. In addition, the IMD 12 shown is merely by way of illustration, and the IMD 12 may have any configuration suitable for use in conjunction with the lead 14 and may be implanted in any suitable location in the patient's body.

The system 10 also includes a converter 30. The converter 30 includes a converter body 32, cuff electrodes 34*a* and 34*b*, a strain relief cuff 36, and a securing mechanism 38. The converter body 32 includes an elongate tube that defines an interior lumen 40. The converter body 32 may be made of a material the same as or substantially similar to the material of the lead 14. In some embodiments, the converter body 32 is made from a polymeric material, such as silicone, polytetrafluoroethylene (PTFE), ethylene tetrafluoroethylene (ETFE), or polyurethane.

The cuff electrodes 34*a* and 34*b* each have a substantially helical shape and are configured to be arranged around excitable tissue such that the interior of the helix is disposed adjacent to the excitable tissue. For example, the cuff electrodes 34*a* and 34*b* may be arranged to encircle a nerve or nerve bundle. In some embodiments, the cuff electrodes 34*a* and 34*b* are comprised of a flexible shape memory material. The cuff electrodes 34*a* and 34*b* also include a conductive material (not shown) that is suitable for carrying electrical energy to the excitable tissue. The conductive material may be arranged along the interior of the helix such that the conductive material is adjacent to the excitable tissue when the cuff electrodes 34*a* and 34*b* are disposed around the excitable tissue. It should be noted that while the cuff electrodes 34*a* and 34*b* are shown, any type of electrode suitable for delivering energy to excitable tissue may alternatively be integrated into the converter 30.

The conductive portions of the cuff electrodes 34*a* and 34*b* are each coupled to the converter body 32 with a conductive element 42. The conductive elements 42 may be made of any suitable conductive material, for example PtIr, stainless steel, or platinized Pt. The conductive elements 42 are each electrically connected to an electrical contact 44 that is secured to the converter body 32. The electrical contacts 44, which may also be comprised of any suitable conductive material, provide a conductive path between the lumen 40 and the exterior of converter body 32. In some embodiments, the electrical contacts 44 have a diameter substantially similar to the diameter of the lumen 40. As will be discussed in more detail below, each of the electrical contacts 44 is arranged along the converter 30 to align with an electrode 20 when the converter 30 is secured to the lead 14. In some embodiments, the electrical contacts 44 are electrically isolated from each other with one or more insulating seals disposed between the electrical contacts 44 in the lumen. The insulating seals may also have a diameter substantially similar to the diameter of the lumen 40.

The strain relief cuff 36 is secured to the converter body 32 by an anchor 46. The anchor may be comprised of a non-conductive material, which may be substantially similar to the material of converter body 32. The strain relief cuff 36 is sized to encircle tissue near the excitable tissue encircled by the cuff electrodes 34*a* and 34*b* to secure the converter 30 relative to the excitable tissue. The strain relief cuff 36 is designed to minimize movement of the cuff electrodes 34*a* and 34*b* relative to the excitable tissue due to voluntary or involuntary movements of the patient. Thus, the strain relief cuff 36 prevents the cuff electrodes 34*a* and 34*b* from becoming dislodged from the excitable tissue to which the cuff electrodes 34*a* and 34*b* are coupled. It should be noted that the strain relief cuff 36 may have alternative configurations, or may be omitted from the converter 30.

The lumen 40 has a diameter substantially similar to the diameter of the lead 14. This allows the lead 14 to be received in the lumen 40 when the converter 30 is secured to the distal end 18 of the lead 14. To secure the converter 30 to the lead 14, the distal end 18 of the lead 14 is placed into the end of the converter body 32 proximate the securing mechanism 38. The converter body 32 then slides over the lead 14 until the securing mechanism 38 aligns with retention cuff 22. The securing mechanism 38 is then actuated or manipulated to engage the securing mechanism 38 with the retention cuff 22, securing the converter 30 relative to the lead 14. In some embodiments, securing mechanism 38 is a set screw that is urged against the retention cuff 22 actuated. It should be noted that the retention cuff 22 is an example of a mechanical element that may be employed to secure the converter 30 to the lead 14, and, in alternative embodiments, may have other forms or may be omitted. In addition, other types of mechanisms may also be employed secure converter 30 relative to lead 14 including, but not limited to, crimps and spring contacts. The converter 30 may also be held relative to the lead 14 from the frictional forces between the lead 14 and the converter body 32.

Figure 1B:
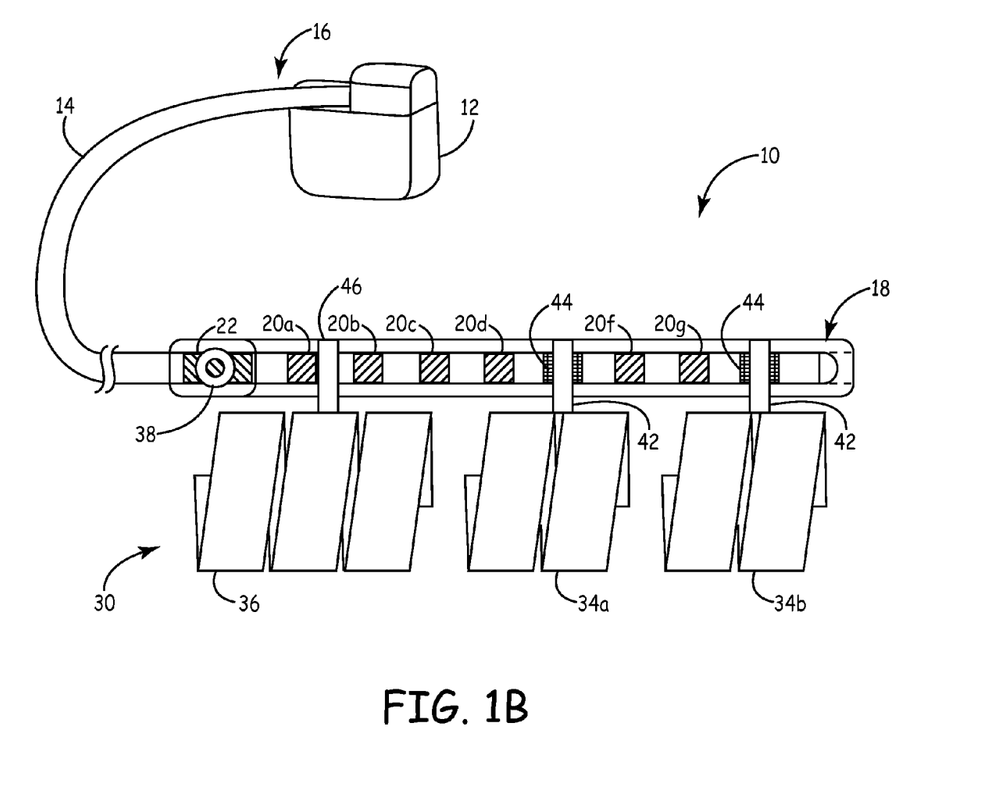
FIG. 1B is a plan view of the converter secured to the distal end of the lead shown in FIG. 1A.

FIG. 1B is a plan view of the converter 30 secured to the lead 14. In the embodiment shown, the electrical contacts 44 are electrically connected to electrodes 20*e* and 20*h* on the lead 14. Thus, the cuff electrode 34*a* receives the electrical energy delivered to the electrode 20*e* by the IMD 12, and the cuff electrode 34*b* receives the electrical energy delivered to the electrode 20*h* by the IMD 12. When the cuff electrodes 34*a* and 34*b* are secured to excitable tissue, the IMD 12 can deliver energy having different characteristics to each of the cuff electrodes 34*a* and 34*b* to provide multi-polar stimulation. In addition, one or both of the cuff electrodes 34*a* and 34*b* may be employed to sense physiological characteristics of the tissue to which it is attached. Furthermore, the cuff electrodes 34*a* and 34*b* may provide combined sensing and stimulation capabilities.

The converter 30 modifies the configuration of the electrodes 20 at the distal end 18 of the lead 14 to provide customized delivery of therapy to excitable tissue. The converter 30 may be employed to adapt a medical device lead designed for one application for use in another application. For example, the electrodes on a lead 14 designed for spinal cord stimulation may be adapted to stimulate the vagus nerve by coupling a converter 30 to the distal end 18 of the spinal cord lead 14. Thus, the converter 30 can transform a lead 14 into a system compatible with specific design and clinical therapy needs. As a result, converters 30 having certain characteristics can be manufactured without redesigning the entire lead 14. In addition, the distal lead converter 30 provides flexibility to clinicians by allowing for converter designs having varying sizes and electrode designs.

In some embodiments, the converter 30 is configured for stimulation or sensing of a nerve or nerve bundle, such as the vagus nerve. The cuff electrodes 34*a* and 34*b* may be arranged around the nerve, with the IMD 12 configured to deliver energy to the cuff electrodes 34*a* and 34*b* to stimulate the nerve. Stimulating the sympathetic and parasympathetic nervous systems can have effects on physiological parameters such as heart rate and blood pressure. In addition, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. The functions associated with the sympathetic and parasympathetic nervous systems are many and can be complexly integrated with each other.

The vagus nerve has afferent properties, such that the neural stimulation is transmitted to the CNS. Vagal stimulation simultaneously increases parasympathetic and decreases sympathetic activity, and is believed to prevent further remodeling or predisposition to fatal arrhythmias in post-MI patients, to help restore autonomic balance and increase heart rate variability (HRV), to increase parasympathetic and reduce sympathetic tone in hypertrophic cardiac myopathy (HCM), neurogenic hypertension, and arrhythmia protection, to reduce anginal symptoms, to increase coronary blood flow (CBF), and to prevent development of congestive heart failure (CHF) following MI. The converter 30 may be configured to stimulate the vagus nerve to provide any of the physiological responses described.

It should be noted that while the converter 30 has been described with regard to use in nerve stimulation and sensing applications, the converter 30 may be configured to adapt the lead 14 for other types of therapies. For example, the converter 30 may be designed to adapt the lead 14 for cardiac sensing and stimulation applications.

Figure 2:
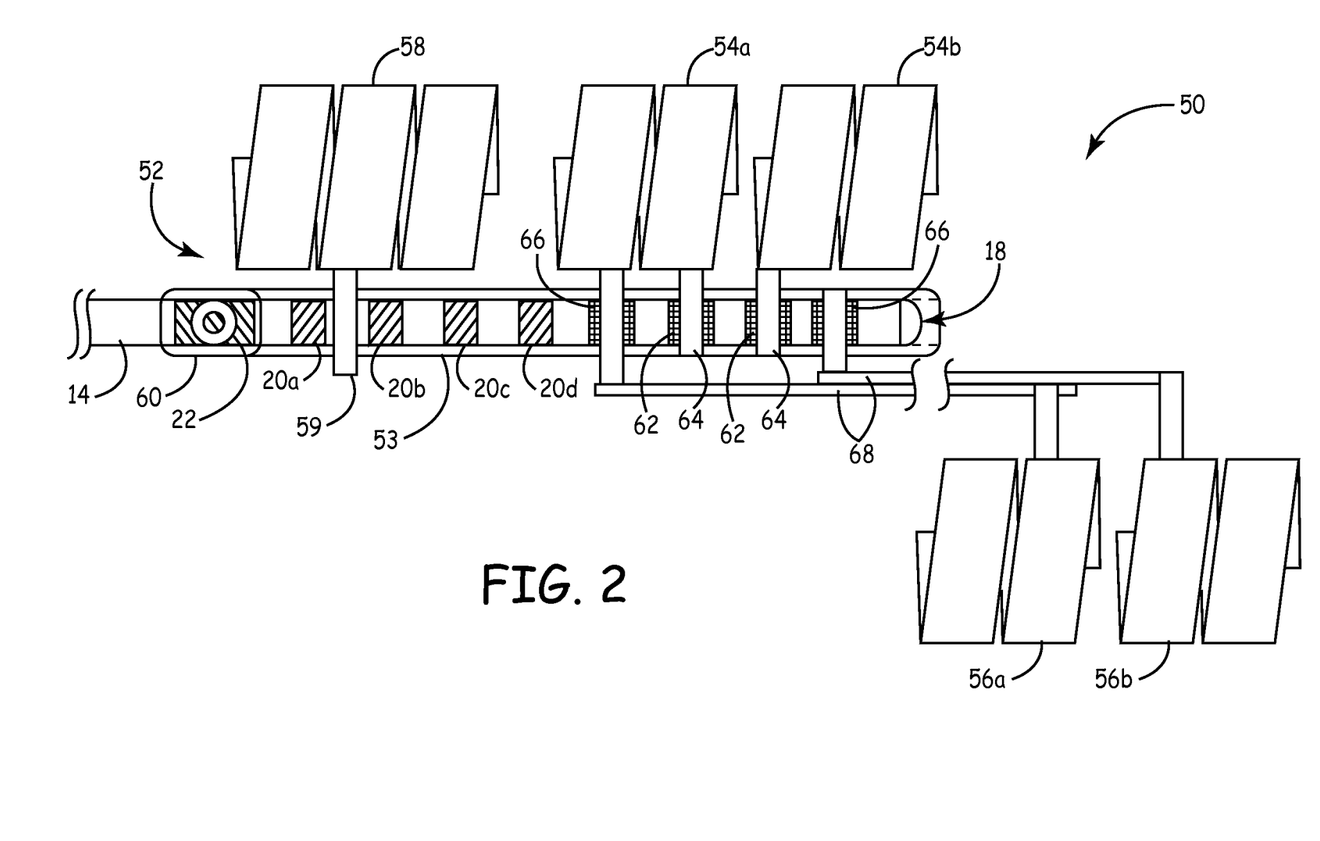
FIG. 2 is a plan view of a system including a converter having cuff electrodes arranged to stimulate excitable tissue in separate physiological locations.

The configuration of cuff electrodes 34a and 34b shown in FIGS. 1A and 1B is merely exemplary, and any arrangement, types, and combinations of electrodes may be included in a distal end converter according to the present subject matter. For example, FIG. 2 is a plan view of a system 50 including a converter 52 secured to the distal end 18 of the lead 14. Only the distal end 18 of the lead 14 is shown in FIG. 2, but it will be appreciated that the proximal end of the lead 14 may be connected to an IMD having characteristics similar to the IMD 12 described above with regard to FIGS. 1A and 1B. The converter 52 includes a converter body 53, proximal cuff electrodes 54a and 54b, distal cuff electrodes 56a and 56b, a strain relief cuff 58, and a securing mechanism 60. The strain relief cuff 58 is secured to the converter body 53 with an anchor 59. The strain relief cuff 58 and the securing mechanism 60 may have configurations and properties similar to the strain relief cuff 36 and the securing mechanism 38, respectively, as described with regard to FIGS. 1A and 1B.

The proximal cuff electrodes 54a and 54b are electrically connected to electrical contacts 62 via conductive elements 64, and the distal cuff electrodes 56a and 56b are connected to electrical contacts 66 via conductive elements 68. The electrical contacts 62 and 66 and the conductive elements 64 and 68 may be made of any conductive material suitable for carrying electrical energy for stimulating excitable tissue. In the embodiment shown, the conductive elements 64 are short to allow the cuff electrodes 54a and 54b to be secured to excitable tissue proximate the converter 52, and the conductive elements 68 are relatively long to allow the cuff electrodes 56a and 56b to be secured to excitable tissue distal from the converter 52. It will be appreciated that the length of conductive elements 64 and/or 68 can be designed to allow for stimulation or sensing of excitable tissue any distance from the converter 52.

When the converter 52 is secured to the distal end 18 of the lead 14 as shown in FIG. 2, the electrical contacts 62 on the converter body 53 are electrically connected to the electrodes 20f and 20g on the lead 14, and the electrical contacts 64 are electrically connected to the electrodes 20e and 20h on the lead 14. Thus, the cuff electrode 54a receives electrical energy delivered to the electrode 20f by the IMD 12, the cuff electrode 54b receives electrical energy delivered to the electrode 20g by the IMD 12, the cuff electrode 56a receives electrical energy delivered to the electrode 20e by the IMD 12, and the cuff electrode 56b receives electrical energy delivered to the electrode 20h by the IMD 12. When the cuff electrodes 54a, 54b, 56a, and 56b are secured to excitable tissue, the IMD 12 can deliver energy having different characteristics to each of the cuff electrodes 54a, 54b, 56a, and 56b. Consequently, different therapies can be delivered to different parts of the patient's anatomy.

Figure 3:
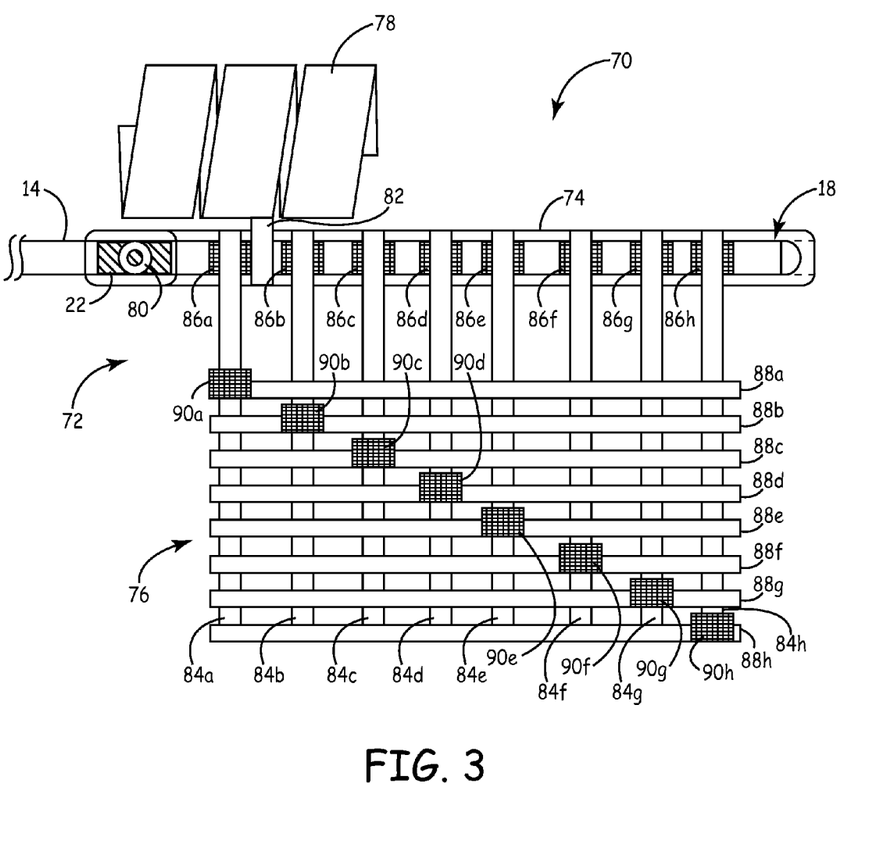
FIG. 3 is a plan view of a system including a converter having an electrode matrix configured to wrap around excitable tissue.

FIG. 3 is a plan view of a system 70 including a converter 72 secured to the distal end 18 of the lead 14. Only the distal end 18 of the lead 14 is shown in FIG. 3, but it will be appreciated that the proximal end of the lead 14 may be connected to an IMD having characteristics similar to the IMD 12 described above with regard to FIGS. 1A and 1B. The converter 72 includes a converter body 74, an electrode matrix 76, a strain relief cuff 78, and a securing mechanism 80. The strain relief cuff 78 is secured to the converter body 74 with an anchor 82. The strain relief cuff 78 and the securing mechanism 80 may have configurations and properties similar to the strain relief cuff 36 and the securing mechanism 38, respectively, as described with regard to FIGS. 1A and 1B.

The electrode matrix 76 includes a plurality of first conductive elements 84a, 84b, 84c, 84d, 84e, 84f, 84g, and 84h electrically connected to electrical contacts 86a, 86b, 86c, 86d, 86e, 86f, 86g, and 86h, respectively, on the converter body 74. The electrode matrix 76 also includes a plurality of second conductive elements 88a, 88b, 88c, 88d, 88e, 88f, 88g, and 88h arranged substantially perpendicular to the first conductive elements 84 to form a matrix pattern. Each of the first conductive elements 84 is electrically connected to a second conductive element 88 with a matrix electrodes 90. More specifically, the matrix electrode 90a electrically connects the first conductive element 84a to the second conductive element 88a, the matrix electrode 90b electrically connects the first conductive element 84b to the second conductive element 88b, and so on. While the electrode matrix 76 is shown with eight matrix electrodes 90 in the pattern shown, it will be appreciated that the electrode matrix 76 can be configured to include any number of matrix electrodes 90 in any pattern.

When the converter 72 is secured to the distal end 18 of the lead 14 as shown in FIG. 3, the electrical contacts 86a-86h on the converter body 74 are electrically connected to the electrodes 20a-20h, respectively, on the lead 14. Thus, the matrix electrode 90a receives electrical energy delivered to the electrode 20a by the IMD 12, the matrix electrode 90b receives the electrical energy delivered to the electrode 20b by the IMD 12, and so on. The electrode matrix 76 may be configured to wrap around excitable tissue, such as a nerve or nerve bundle, to deliver stimulation energy. When the electrode matrix 76 is secured to excitable tissue, the IMD 12 can deliver energy having different characteristics to portions of the excitable tissue. For example, the energy delivered to each of the matrix electrodes 90 can be controlled to provide particular electrical or physiological responses, such as current steering, afferent/efferent steering, and the like.

Figure 4:
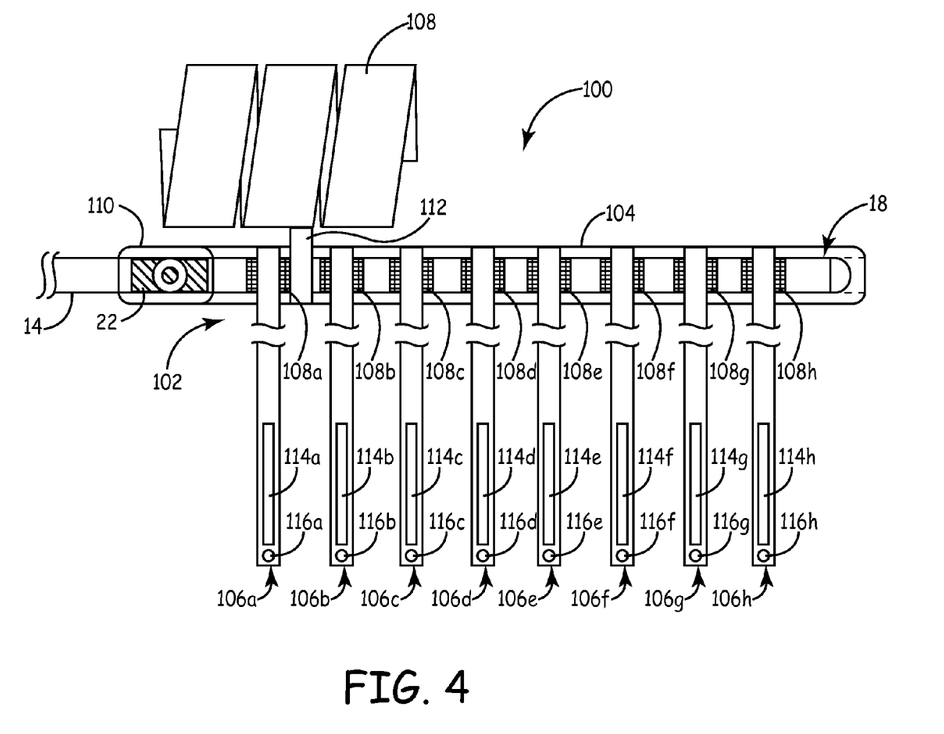
FIG. 4 is a plan view of a system including a converter having wire electrodes configured for suturing to excitable tissue.

FIG. 4 is a plan view of a system 100 including a converter 102 secured to the distal end 18 of the lead 14. Only the distal end 18 of the lead 14 is shown in FIG. 4, but it will be appreciated that the proximal end of the lead 14 may be connected to an IMD having characteristics similar to the IMD 12 described above with regard to FIGS. 1A and 1B. The converter 102 includes a converter body 104, wire electrodes 106a, 106b, 106c, 106d, 106e, 106f, 106g, and 106h, a strain relief cuff 108, and a securing mechanism 110. The strain relief cuff 108 is secured to the converter body 104 with an anchor 112. The strain relief cuff 108 and the securing mechanism 110 may have configurations and properties similar to the strain relief cuff 36 and the securing mechanism 38, respectively, as described with regard to FIGS. 1A and 1B.

The wire electrodes 106a, 106b, 106c, 106d, 106e, 106f, 106g, and 106h are electrically connected to electrical contacts 108a, 108b, 108c, 108d, 108e, 108f, 108g, and 108h, respectively, on the converter body 104. The wire electrodes 106a-106h and the conductive elements 108a-108h may be made of any conductive material suitable for carrying electrical energy for stimulating excitable tissue. The wire electrodes 106a-106h each include a tissue contact pad 114a-114h, respectively, that is positionable adjacent excitable tissue and provides a surface for distributing energy to the excitable tissue. The wire electrodes 106a-106h also each include a suture hole 116a-116h, respectively. It should be noted that while eight wire electrodes 106a-106h having substantially similar lengths are shown, any number of wire electrodes having substantially similar or varying lengths may alternatively be coupled to the converter 102.

When the converter 102 is secured to the distal end 18 of the lead 14 as shown in FIG. 4, the electrical contacts 108a-108h on the converter body 104 are electrically connected to the electrodes 20a-20h, respectively, on the lead 14. Thus, the wire electrode 106a receives electrical energy delivered to the electrode 20a by the IMD 12, the wire electrode 106b receives the electrical energy delivered to the electrode 20b by the IMD 12, and so on. Each wire electrode 106 is secured to the excitable tissue such that the associated tissue contact pad 114 is held adjacent to the excitable tissue. In some embodiments, each wire electrode 106 is secured to the excitable tissue by suturing through the suture hole 116 associated with the wire electrode 106. When the wire electrodes 106a-106h are secured to excitable tissue, the IMD 12 can deliver energy having different characteristics to portions of the same excitable tissue or to tissue located physiologically apart from each other.

Figure 5:
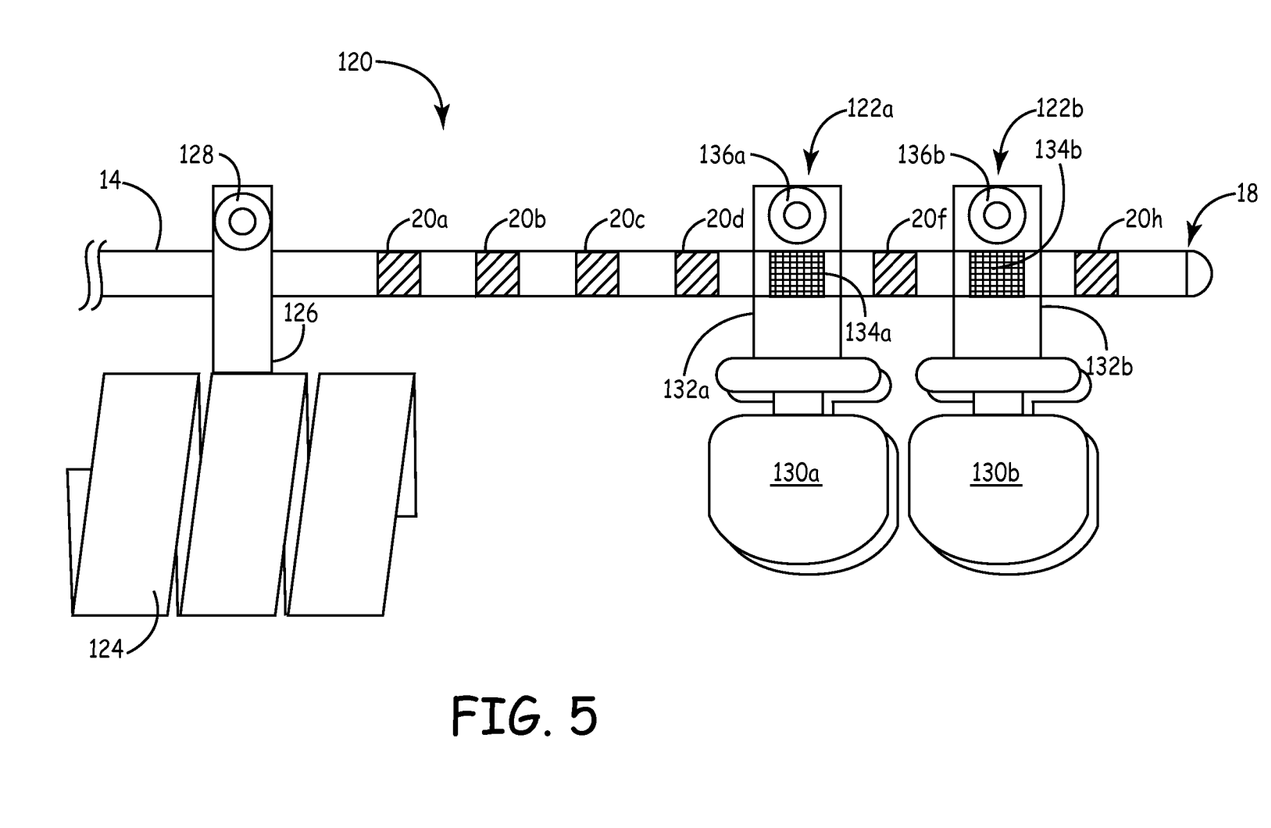
FIG. 5 is a plan view of a system including a plurality of converters coupled to clamshell electrodes and configured for securing to a lead.

The embodiments described thus far have related to converters in the form of a longitudinal tube or sleeve configured to be placed over the distal end 18 of the lead 14. However, alternative configurations for modifying the electrode configuration of a medical device lead are also possible. For example, FIG. 5 is a plan view of a system 120 including electrode converters 122a and 122b and a strain relief cuff 124 secured to the lead 14. The strain relief cuff 124 is coupled to the lead 14 with a band 126 that is secured around the lead 14 with a securing mechanism 128, such as a snap, crimp, weld, set screw, or the like. The strain relief cuff 124 may have a configuration and properties similar to the strain relief cuff 36 as described with regard to FIGS. 1A and 1B.

The electrode converters 122a and 122b include clamshell electrodes 130a and 130b, respectively, coupled to the lead 14 with bands 132a and 132b, respectively. The clamshell electrode 130a and 130b are electrically connected to electrical contacts 134a and 134b, respectively, on the bands 132a and 132b, respectively. The clamshell electrodes 130a and 130b and the conductive elements 108a-108h may be made of any conductive material suitable for carrying electrical energy for stimulating excitable tissue. In some embodiments, the bands 132a and 132b are also comprised of a conductive material to electrically connect the clamshell electrodes 130a and 130b to the electrical contacts 134a and 134b, respectively. In other embodiments, the clamshell electrodes 130a and 130b are connected to the electrical contacts 134a and 134b with a separate conductive element not shown in FIG. 5. The bands 132a and 132b are secured to the lead 14 with securing mechanisms 136a and 136b, respectively, such as a snap, crimp, weld, set screw, or the like.

When the electrode converters 122a and 122b are secured to the distal end 18 of the lead 14 as shown in FIG. 5, the electrical contacts 134a and 134b are electrically connected to the electrodes 20e and 20g, respectively, on the lead 14. Thus, the clamshell electrode 130a receives electrical energy delivered to the electrode 20e by the IMD 12, and the clamshell electrode 130b receives the electrical energy delivered to the electrode 20g by the IMD 12. When implanted, each clamshell electrode 130a and 130b is positioned adjacent to excitable tissue to be stimulated, and the IMD 12 can deliver energy having different characteristics to the excitable tissue adjacent the clamshell electrodes 130a and 130b.

Figure 6:
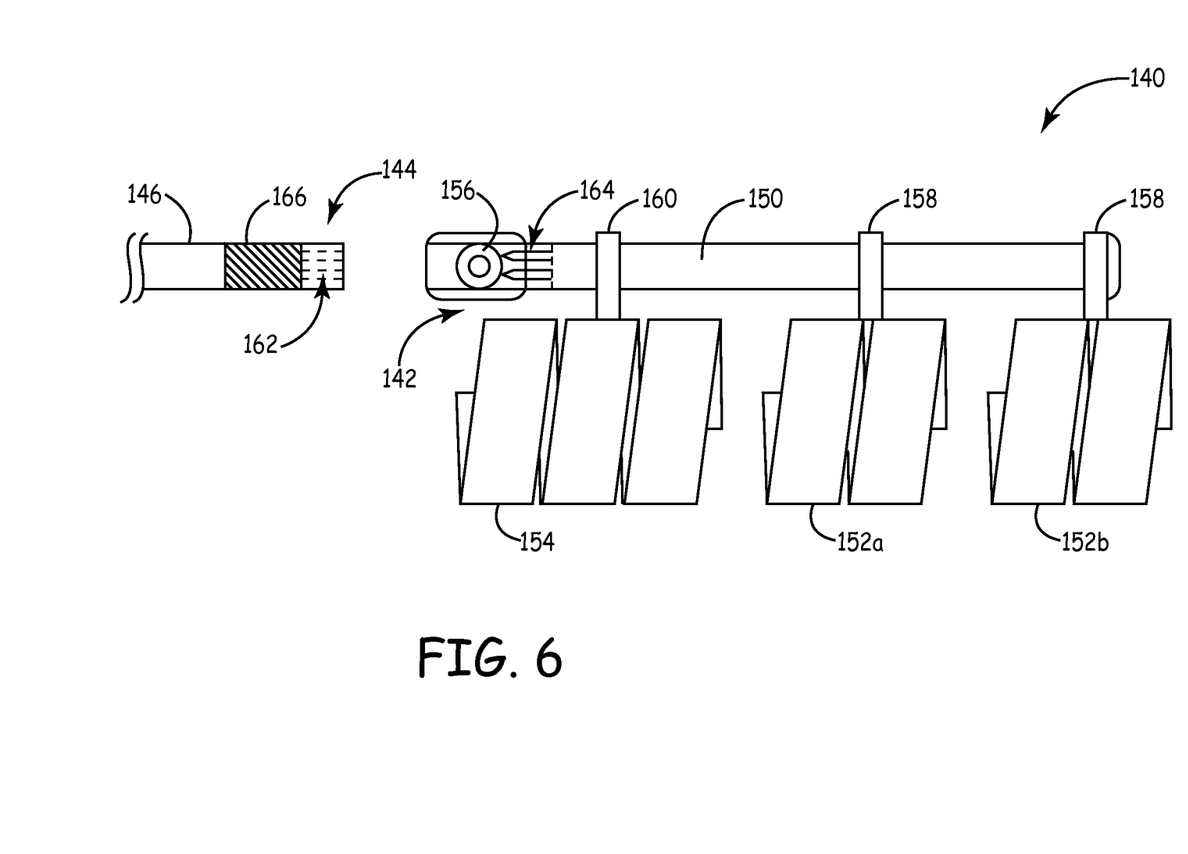
FIG. 6 is a plan view of a system including a converter including male connectors configured to mate with female connectors on a lead.

FIG. 6 is a plan view of a system 140 including a converter 142 securable to the distal end 144 of a lead 146. Only the distal end 144 of the lead 146 is shown in FIG. 6, but it will be appreciated that the proximal end of the lead 146 may be connected to an IMD having characteristics similar to the IMD 12 described above with regard to FIGS. 1A and 1B. The converter 142 includes a converter body 150, cuff electrodes 152a and 152b, a strain relief cuff 154, and a securing mechanism 156. The cuff electrodes 152a and 152b are coupled to the converter body 150 via conductive elements 158, and the strain relief cuff 154 is secured to the converter body 150 with an anchor 160. The cuff electrodes 152a, 152b, and the conductive elements 154 may have configurations and properties similar to cuff electrodes 34a, 34b and conductive elements 42 described with regard to FIGS. 1A and 1B. In addition, the strain relief cuff 154 and the securing mechanism 156 may have configurations and properties similar to the strain relief cuff 36 and the securing mechanism 38, respectively, as described with regard to FIGS. 1A and 1B.

In the embodiment shown in FIG. 6, the distal end 144 of the lead 146 includes one or more female connectors 162, and the end of converter 142 proximate the securing mechanism 156 includes one or more male connectors 164. To secure the converter 142 to the distal end 144 of the lead 146, the one or more male connectors 164 are inserted into the corresponding one or more female connectors 162. The securing mechanism 156 may then be actuated or manipulated to engage the securing mechanism 156 with the retention cuff 166 on the lead 146, securing the converter 142 relative to the lead 146. In an alternative embodiment, the converter 142 includes female connectors and the distal end 144 of the lead 146 includes male connectors.

When the one or more male connectors 164 are mated with the one or more female connectors 162, an electrical connection is provided between the IMD 12 at the proximal end of the lead 146 and the converter 150. Each of the one or male connectors 164 is electrically connected to one of the conductive elements 158. Thus, electrical energy can be provided from the IMD 12 to each of the cuff electrodes 152a and 152b. When the cuff electrodes 152a and 152b are secured to excitable tissue, the IMD 12 can deliver energy having different characteristics to each of the cuff electrodes 152a and 152b. Consequently, different therapies can be delivered to different parts of the patient's anatomy. It should be noted that while two cuff electrodes 152a and 152b are shown in FIG. 6, the converter 142 can be configured to accommodate other numbers or types of electrodes based on the number of male/female connections available at the interface between converter 142 and lead 146.

In summary, the present invention relates to a system for delivering signals between a pulse generator and tissue. The system includes a lead having a lead body and one or more lead electrodes at a distal end of the lead body. The one or more electrodes are electrically connectable to the pulse generator at a proximal end of the lead body via one or more conductors extending through the lead body. A converter, which is removably securable to the distal end of the lead body, includes one or more converter electrodes. Each converter electrode is connected to an electrical contact that is arranged on the converter to electrically connect the converter electrode to at least one of the one or more lead electrodes. A converter securable to the lead distal end can transform the lead into a system compatible with specific design and clinical therapy needs. As a result, converters having certain characteristics can be manufactured without redesigning the entire lead. In addition, the distal lead converter provides flexibility to clinicians by allowing for converter designs having varying sizes and electrode designs. Furthermore, the converter allows explant of only the lead body or converter in the case of malfunction of either of these components, rather than replacement of the entire lead.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A system for delivering signals between a pulse generator and tissue, the system comprising:
   a lead including a lead body and one or more lead electrodes at a distal end of the lead body that are electrically connectable to the pulse generator at a proximal end of the lead body via one or more conductors extending through the lead body; and
   a converter removably securable to the distal end of the lead body and including one or more converter electrodes, wherein each converter electrode is connected to an electrical contact that is arranged on the converter to interface with, and electrically connect the converter electrode to, at least one of the one or more lead electrodes.

2. The system of claim 1, wherein the one or more converter electrodes are separately controllable with the pulse generator.

3. The system of claim 1, wherein the electrical contacts are arranged to facilitate multi-polar communication through the one or more converter electrodes.

4. The system of claim 1, wherein at least one of the one or more converter electrodes comprises a cuff configured to wrap around the tissue.

5. The system of claim 1, wherein at least one of the one or more converter electrodes comprises a wire configured for securing to the tissue.

6. The system of claim 1, wherein the lead and converter are configured to frictionally secure the converter to the lead.

7. The system of claim 1, and further comprising:
   a securing element coupled to the converter and configured to secure the converter to the tissue.

8. The system of claim 7, wherein the securing element comprises a strain relief cuff.

9. The system of claim 1, wherein the converter comprises a converter body including a lumen sized to closely fit around the distal end of the lead body.

10. A converter for modifying a configuration of lead electrodes at a distal end of a medical device lead, the converter comprising:
    a converter body removably securable to the distal end of the medical device lead;
    one or more converter electrodes coupled to the converter body; and
    one or more electrical contacts, wherein each electrical contact is arranged to interface with one of the lead electrodes to electrically connect one of the one or more converter electrodes to the one of the lead electrodes.

11. The converter of claim 10, wherein the converter body comprises an elongated element including a lumen sized to closely fit around the distal end of the medical device lead.

12. The converter of claim 10, and further comprising:
    a securing element coupled to the converter body and configured to secure the converter to tissue.

13. The converter of claim 10, wherein at least one of the one or more converter electrodes comprises a cuff configured to wrap around excitable tissue.

14. The converter of claim 10, wherein the converter body includes a securing element configured to mechanically engage a receiving element on the medical device lead.

15. The converter of claim 10, wherein the converter body includes one or more apertures arranged to expose at least a portion of one or more of the lead electrodes through the converter body.

16. An implantable medical device comprising:
    a pulse generator;
    a lead including a proximal end adapted to be connected to the pulse generator, and a distal end including one or more lead electrodes adapted to deliver electrical signals from the pulse generator; and
    a converter removably secured to the distal end of the lead body and including one or more converter electrodes, wherein each converter electrode is connected to an electrical contact that is arranged to interface with one of the one or more lead electrodes to electrically connect the converter electrode to the one of the one or more lead electrodes.

17. The implantable medical device of claim 16, wherein the electrical contacts are arranged to facilitate multi-polar communication through the one or more converter electrodes.

18. The implantable medical device of claim 16, wherein pulse generator is configured to separately control the one or more converter electrodes.

19. The implantable medical device of claim 16, and further comprising:
    a securing element coupled to the converter and configured to secure the converter to tissue.

20. The implantable medical device of claim 16, wherein the converter comprises a converter body including a lumen sized to closely fit around the distal end of the medical device lead.

21. The implantable medical device of claim 16, wherein at least one of the one or more converter electrodes comprises a cuff configured to wrap around excitable tissue.

* * * * *